(12) United States Patent
Qiu et al.

(10) Patent No.: US 10,212,957 B2
(45) Date of Patent: Feb. 26, 2019

(54) METHOD FOR PREPARING OIL-DISPERSIBLE CAROTENOID PREPARATION

(71) Applicants: ZHEJIANG NEW WEIPU ADDITIVE CO., LTD., Shaoxing, Zhejiang Province (CN); ZHEJIANG UNIVERSITY, Hangzhou, Zhejiang Province (CN); ZHEJIANG NHU COMPANY LTD., Shaoxing, Zhejiang Province (CN)

(72) Inventors: Dan Qiu, Ningbo (CN); Lifang Shi, Shaoxing (CN); Jiandong Li, Shaoxing (CN); Zhirong Chen, Hangzhou (CN); Jiachao Zhou, Shaoxing (CN)

(73) Assignees: ZHEJIANG UNIVERSITY, Hangzhou (CN); ZHEJIANG NHU COMPANY LTD., Shaoxing (CN)

( * ) Notice: Subject to any disclaimer, the term of this patent is extended or adjusted under 35 U.S.C. 154(b) by 248 days.

(21) Appl. No.: 14/902,553

(22) PCT Filed: Jun. 3, 2014

(86) PCT No.: PCT/CN2014/079069
§ 371 (c)(1),
(2) Date: Dec. 31, 2015

(87) PCT Pub. No.: WO2015/003536
PCT Pub. Date: Jan. 15, 2015

(65) Prior Publication Data
US 2016/0374375 A1  Dec. 29, 2016

(30) Foreign Application Priority Data

Jul. 9, 2013 (CN) .......................... 2013 1 0286768

(51) Int. Cl.
*A23L 5/44* (2016.01)
*A23L 33/105* (2016.01)

(52) U.S. Cl.
CPC ............... *A23L 5/44* (2016.08); *A23L 33/105* (2016.08); *A23V 2002/00* (2013.01)

(58) Field of Classification Search
CPC ...... A23L 5/44; A23L 33/105; A23V 2002/00
See application file for complete search history.

(56) References Cited

U.S. PATENT DOCUMENTS

| 2003/0031706 A1* | 2/2003 | Runge ................... A61K 31/07 424/456 |
| 2012/0018912 A1* | 1/2012 | Chen .................... A61K 8/0241 264/5 |

FOREIGN PATENT DOCUMENTS

| CN | 101549273 A | 10/2009 |
| CN | 102525923 A | 7/2012 |

* cited by examiner

*Primary Examiner* — Subbalakshmi Prakash
(74) *Attorney, Agent, or Firm* — Jiwen Chen

(57) ABSTRACT

Disclosed in the present invention is a method for preparing an oil-dispersible carotenoid preparation, comprising (by weight parts): mixing 100 parts of carotenoid microcapsule, 100-400 parts of vegetable oil and 0.1-1 part of oil-soluble antioxidant; and grinding the mixture in a colloid mill in a nitro—gen atmosphere and at 10-30° C. to obtain a uniform oil-dispersible carotenoid preparation, wherein the preparation contains 2%-14% carotenoid with an average particle size of up to 0.1-1 μm, and 100 parts of carotenoid microcapsule contains 10.5-35.8 parts carotenoid, 0.1-1 part of water-soluble antioxidant, and the remainder is a water-soluble colloid. The advantages of the present invention lie in that the oil-dispersible form has a high stability as the surface of the carotenoid particles is still protected with a dense water-soluble colloid, and that an oil-dispersible caro- (Continued)

tenoid preparation containing carotenoid with a content of up to 2%-14% and an average particle size of only 0.1-1 μm can be prepared.

8 Claims, 2 Drawing Sheets

METHOD FOR PREPARING OIL-DISPERSIBLE CAROTENOID PREPARATION

This is a U.S. national stage application of PCT Application No. PCT/CN2014/079069under 35 U.S.C. 371, filed Jun. 3, 2014 in Chinese, claiming the priority benefit of Chinese Application No. 201310286768.5, filed Jul. 9, 2013, which is hereby incorporated by reference.

FIELD OF THE INVENTION

The present invention relates to a method for preparing carotenoid, especially a method for preparing an oil-dispersible carotenoid preparation.

BACKGROUND OF THE INVENTION

Carotenoids exist extensively in the nature and current commercial carotenoid products mainly include beta-carotene, astaxanthin, lycopene, canthaxanthin and lutein, etc. which are widely used in the food, cosmetics, fodder, pharmaceutical industries and other fields as nutrient supplements and colorants. Carotenoids are insoluble in water, rarely soluble in oil, quite sensitive to light, heat and oxygen and cannot be directly used. Generally, carotenoids shall be refined and made into different preparation forms before application in pharmaceutical, health care product, food and fodder fields, since carotenoid preparations can significantly improve bioavailability, pigmentation effect and reduce the dosage.

Reports on preparation methods of carotenoids mainly include the following methods:

WO91/06292 and WO94/19411 introduce a method for preparing water-dispersible carotenoid powders by grinding beta-carotene into 2~10 μm particles with a colloid mill and then drying.

U.S. Pat. No. 3,998,753 records a method for preparing water-dispersible carotenoids with a particle size of less than 1 μm. In such method, carotenoids and other additives are first made into an organic solvent solution, and then added into a water solution containing gelatin, disperser and stabilizer to form emulsion after high-speed shearing; the organic solvent is removed, spray drying and then the required product can be obtained.

According to the method for preparing water-dispersible carotenoid powders in EP0065193, carotenoids are dissolved in a volatile water-mixable solvent within 10 seconds under 50~200° C. and then quickly mixed with water solution containing protective colloid under 0~50° C., wherein carotenoids are dispersed in the protective colloid in the size of less than 0.5 μm and carotenoid powders can be obtained after removing the solvent and drying. In CN102361561A, an instant stable suspension for some amorphous carotenoid particles is obtained with similar technology.

CN102281859A discloses a method for preparing an emulsion composition mainly by mixing an oil phase containing carotenoids with an aqueous phase containing various emulsifiers; in CN101312655B, products are also obtained with similar technology through spray drying of emulsion.

CN1233169A reports two supercritical fluid treatment technologies: in technology A, carotenoids are first dissolved in supercritical dimethyl ether under high temperature and high pressure, and then rapidly decompressed to obtain powder-like carotenoid particles; in technology B, carotenoids are first dissolved in subcritical or supercritical compressed gas under high temperature and high pressure, then such solution is dispersed in other ingredients, and then the compressed gas was removed in such mixture to obtain powder-like preparations.

U.S. Pat. No. 6,056,791 also reports a technology, in which carotenoids and a supercritical fluid are mixed under a certain pressure until a solution containing 5%-90% supercritical fluid is formed. Melting point of the selected supercritical fluid shall be at least 40° C. lower than that of the carotenoid. Then, the temperature is adjusted to 50° C. higher or lower than the melting point of the supercritical fluid and the pressure is reduced to atmospheric pressure. Under such conditions, the supercritical fluid will be gasified quickly and the particle size of carotenoid can reach 0.7 μm-5 μm.

DE2943267 mentions a method for preparing solid drugs by dissolving beta-carotene in a supercritical fluid, quickly decompressing to obtain beta-carotene in fine particle and then adding other ingredients.

The Applicant has also successively applied for a series of patents, including a method for preparing water-dispersible carotenoid powder (Patent Publication No.: CN1836652A) applied in 2005, a method for preparing high all-trans beta-carotene (Patent Publication No.: CN101016259A) applied in 2007, a method for preparing a nano-dispersed high all-trans carotenoid microcapsule (Patent Publication No.: CN101549273B) applied in 2009 and a method for preparing an isomer ratio controllable carotenoid microcapsule (Patent Publication No.: CN101879428A) applied in 2010.

The aforesaid forms are all emulsion, microcapsule and other water-dispersible or solid dosage forms and are difficult to be applied in oil phase system. Reports on preparation methods of dosage forms applied in oil phase system mainly are:

CN102341002A relates to obtaining 0.01~10 g/kg carotenoid vegetable oil solution with maximum concentration of only 1% by processing carotenoid oil suspension through changing the heating technology, wherein carotenoid has very poor chemical stability in oil solution with likely side reactions.

CN1185433 reports a liquid-oil-mixable carotenoid preparation, wherein carotenoid water-dispersible phase is added into oil phase to make W/O emulsion, in which the aqueous phase liquid drop size approaches to 1 μm and carotenoid particle size reaches to 0.1~0.2 μm. However, due to a large content of solvent, emulsifier and excipients, the maximum content of carotenoid is only around 1% and the complicated emulsion system has a poor stability in application and is unable to adapt to high temperature, high pressure and other severe processing conditions.

In CN101611876, carotenoids and soybean phospholipids are first grinded into an emulsion particle solution and then mixed with vegetable oil for dilution and smashing to obtain particle emulsion, wherein the carotenoid particle size is only 5~10 μm;

Currently, the general carotenoid oil suspension fluid is obtained by directly mixing and grinding carotenoid crystals with vegetable oil. In recent years, improvements are made on such basis in related patents. In CN101828693A, carotenoid oil suspension fluid with particle size of around 10 μm is obtained by processing carotenoid crystals with tetrahydrofuran, ethanol and vegetable oil, etc; in CN102552173A, carotenoid oil suspension fluid with average particle size of less than 5 μm is obtained by putting carotenoid solution into vegetable oil via atomization. However, the uniformity and carotenoid particle size in these 2 technologies cannot reach the emulsion level.

In conclusion, the water-dispersible form of carotenoid can generally reach a smaller particle size and have good stability in the form of microcapsule; while the oil-dispersible form mostly has a larger particle size and the effective substance is directly exposed to dispersion medium with poor stability, wherein a smaller particle size can be realized in only a few methods and the maximum content is only around 1% due to formula restrictions with no dense protective layer on carotenoids.

DISCLOSURE OF THE INVENTION

Technical Problems

The present invention discloses a method for preparing an oil-dispersible carotenoid preparation which comprises a carotenoid content of up to 2%~14% with an average carotenoid particle size of 0.1~1 μm and a dense water-soluble colloid protective layer on the surface of carotenoid particles.

Solution to Problem

A method for preparing an oil-dispersible carotenoid preparation, comprising (by weight parts):

Mixing 100 parts of carotenoid microcapsule, 100~400 parts of vegetable oil and 0.1~1 part of antioxidant B, and grinding the mixture in a colloid mill for 1~5 times in a nitrogen atmosphere at 10-30° C. to obtain a uniform oil-dispersible carotenoid preparation, wherein the average particle size of carotenoid is up to 0.1~1 μm;

The 100 parts of carotenoid microcapsule contains 10.5~35.8 parts of carotenoid, 0.1~1 part of antioxidant A and the remaining is a water-soluble colloid; the preparation technology of carotenoid microcapsule refers to the method as described in CN1836652A or CN101549273B.

The antioxidant A is vitamin C, vitamin C sodium, iso-vitamin C or iso-vitamin C sodium;

The antioxidant B is tocopherol, ethoxyquin, 2,6-di-tert-butyl-4-methylphenol (BHT) or tert-butylhydroquinone (TBHQ);

The carotenoid is beta-carotene, astaxanthin, lycopene, canthaxanthin or lutein;

The water-soluble colloid is gelatin, octenyl succinic starch ester or Arabic gum;

The vegetable oil is soybean oil, corn oil, sunflower seed oil, peanut oil or salad oil.

The content of carotenoid in the oil-dispersible carotenoid preparation is measured and determined with ultraviolet spectrum, and the particle size of carotenoid is measured and determined with laser particle analyzer in the following specific method: filtering the oil-dispersible carotenoid preparation with a 0.3 μm millipore filter, collecting particles in the oil, adding water to disperse particles and taking an aqueous phase sample for detection with a laser particle analyzer.

Beneficial Effects of the Invention

The advantages of the present invention lie in that the oil-dispersible form has a high stability as the surface of the carotenoid particles is still protected with a dense water-soluble colloid, and that an oil-dispersible carotenoid preparation containing carotenoid with a content of up to 2%-14% and an average particle size of only 0.1-1 can be prepared with strong practicability.

PREFERRED EMBODIMENT OF THE INVENTION

Embodiment 1

Figure 1:
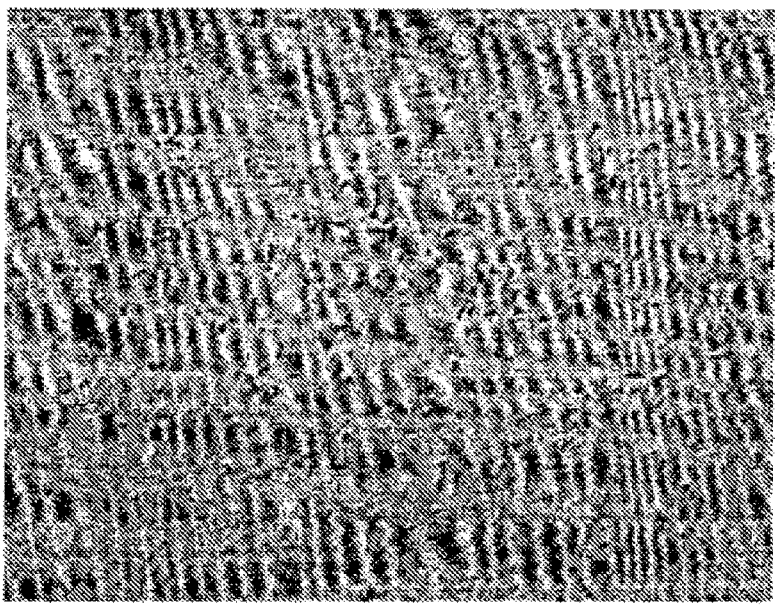
FIG. 1 shows the optical microscopic picture of an oil-dispersible astaxanthin form prepared in embodiment 1 at the amplification factor of 200.

20 g astaxanthin coarse crystal was dissolved in 3 L dichloromethane to make astaxanthin solution; the astaxanthin solution was slowly added into a vessel containing 20 L ethanol in spraying form and the spraying speed was adjusted to make the particle size of precipitated amorphous astaxanthin particles less than 2 μm; a 0.3 μm millipore filter was used after spraying, the filter cake was washed with ethanol and pressed to dry to obtain a super refined astaxanthin powder filter cake; such filter cake was mixed with a 1 L water solution which contains 0.1 g vitamin C and 89.4 g gelatin, stirred and pulped, then was put in a high pressure homogenizer for 5 hours when the emulsion desolventized first in vacuum, and then 100 g astaxanthin microcapsule containing 10.5 g astaxanthin can be obtained after spray drying.

100 g astaxanthin microcapsule was mixed with 100 g soybean oil containing 0.2 g tocopherol and the mixture was grinded in a colloid mill for 3 times in a nitrogen atmosphere at 30° C. to obtain a uniform oil-dispersible astaxanthin preparation which contains 5.0% astaxanthin, wherein the average particle size of astaxanthin was up to 0.82 μm.

Comparison Example 25.3 g astaxanthin coarse crystal was mixed with 475 g soybean oil containing 0.1 g tocopherol and the mixture was grinded in a colloid mill for 3 times in a nitrogen atmosphere at 30° C. to obtain a uniform oil-dispersible astaxanthin preparation which contains 5.0% astaxanthin, wherein the average particle size of astaxanthin was up to 1.21 μm.

Test Embodiment

Figure 2:
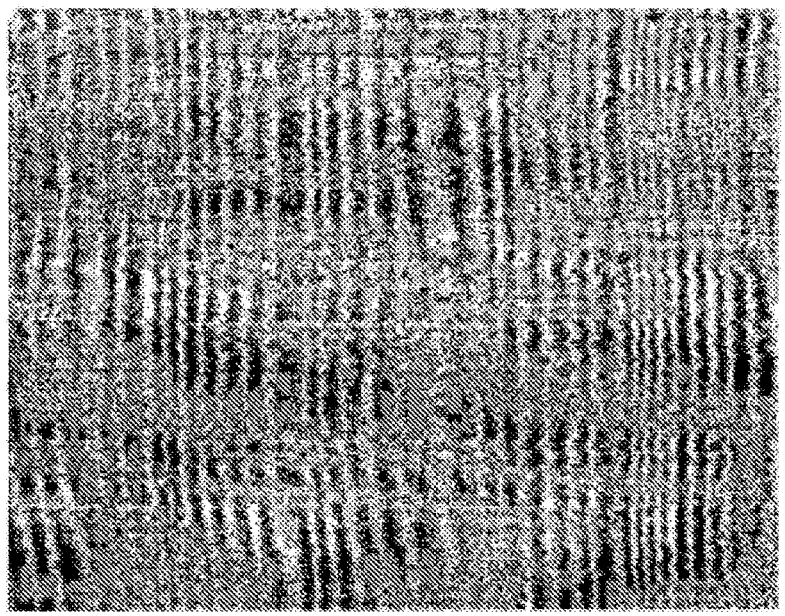
FIG. 2 shows the optical microscopic picture of an oil-dispersible astaxanthin form prepared in a contrasting embodiment at the amplification factor of 200.

The oil-dispersible astaxanthin preparation obtained in embodiment 1 and the oil-dispersible astaxanthin preparation obtained in the contrasting embodiment respectively were observed under an optical microscope with amplification factor of 200, microscopic pictures were obtained in FIG. 1 and FIG. 2. FIG. 1 shows the microscopic picture of the oil-dispersible astaxanthin preparation obtained in embodiment 1, wherein astaxanthin was obviously covered by coating material and the average size of particles dispersed in oil was 30.34 μm, and the average particle size of astaxanthin in aqueous phase was detected as 0.82 μm after sampling, filtration and dispersing with water; FIG. 2 shows the microscopic picture of the oil-dispersible astaxanthin preparation obtained in the contrasting embodiment, wherein astaxanthin existed in a crystal form with average particle size of up to 1.21 μm.

Figure 3:
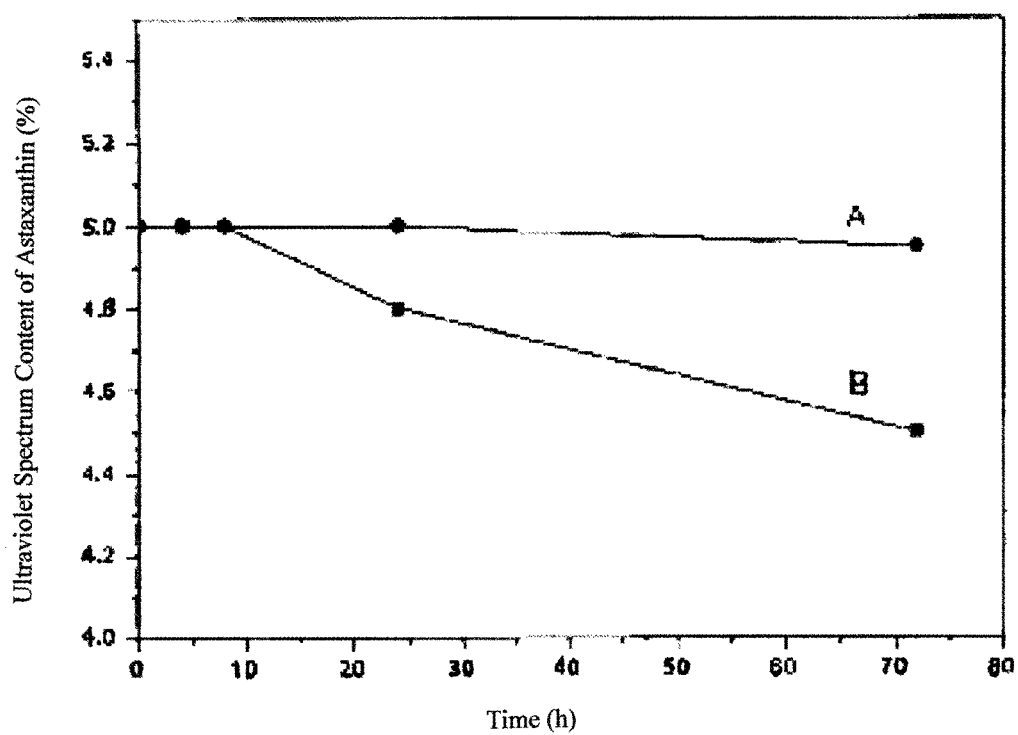
FIG. 3 shows the comparison of the thermal stability of the oil-dispersible astaxanthin form (A) prepared in embodiment 1 and the oil-dispersible astaxanthin form (B) prepared in a contrasting embodiment.

The oil-dispersible astaxanthin preparation obtained in embodiment 1 and the oil-dispersible astaxanthin preparation obtained in the contrasting embodiment were respectively put under 90° C. for accelerated degradation test and their stability was compared by measuring the content of astaxanthin in samples at different times. As shown in FIG. 3, the horizontal ordinate stands for the time and the vertical ordinate stands for the content of astaxanthin in samples determined with ultraviolet spectroscopy; the curve A stands for the oil-dispersible astaxanthin preparation obtained in embodiment 1 and the curve B stands for the oil-dispersible astaxanthin preparation obtained in the contrasting embodiment. The oil-dispersible astaxanthin preparation obtained in the contrasting embodiment started to degrade obviously after heating for 8 h, while the content of astaxanthin in the oil-dispersible astaxanthin preparation obtained in embodiment 1 still did not decrease greatly after 72 hours, which indicated that the thermal stability of the oil-dispersible astaxanthin preparation obtained in embodiment 1 was significantly improved.

Embodiment 2

36.5 kg beta-carotene crystal and 260 kg dichloromethane were grinded in a sand mill to obtain a beta-carotene suspension liquid with an average particle size of 3 μm; 1 kg vitamin C sodium and 63.2 kg octenyl succinic starch ester were dissolved in 200 kg water and kept warm at 40° C. for later use.

The beta-carotene suspension liquid was fed into the bottom of a 4 L, 4-storeyed stirring vessel with height-diameter ratio of 4 via a pulp pump at a flow rate of 8 kg/h, dichloromethane which is preheated to 37° C. by a coiler preheater was fed into the bottom of the stirring vessel at a flow rate of 200 kg/h as well at the same time, the temperature in the vessel was controlled at 38° C. and pressure at 0.25 Mpa, was stay for about 15 minutes and a sample was taken for analysis to know that the dissolution into beta-carotene solution has been completed; the beta-carotene solution and isopropanol (at a flow rate of 1000 kg/h) was led into an over-gravity rotary bed crystallization device at the same time and the rotating speed was controlled at 3000 revolution/min to obtain a beta-carotene dispersion liquid at a flow rate of 1200 kg/h; and then such beta-carotene dispersion liquid was decompressed in a falling-film evaporator to remove most solvents to obtain a beta-carotene isopropanol dispersion liquid at a flow rate of 7 kg/h.

The above beta-carotene isopropanol dispersion liquid was led into another over-gravity rotary bed pulping device with a pump at a flow rate of 7 kg/h, and the prepared octenyl succinic starch ester solution was fed into such an over-gravity rotary bed pulping device at a flow rate of 27 kg/h at the same time to obtain a pulp fluid at a flow rate of around 35 kg/h; the pulp fluid was directly spray dried to obtain 100 kg beta-carotene microcapsule which contains 35.8 kg beta-carotene.

100 kg beta-carotene microcapsule was mixed with 150 kg corn oil containing 1 kg ethoxyquin and the mixture was grinded in a colloid mill for 5 times in a nitrogen atmosphere at 10° C. to obtain a uniform oil-dispersible beta-carotene preparation which contained 14.0% beta-carotene, wherein the average particle size of beta-carotene was up to 0.31 μm.

Embodiment 3

50 g canthaxanthin coarse crystal was dissolved in 2 L chloroform to make canthaxanthin solution; the canthaxanthin solution was slowly added into a vessel containing 20 L 95% ethanol in spraying form and the spraying speed was adjusted to make the particle size of precipitated amorphous canthaxanthin particles less than 2 μm; filtered with a 0.3 μm millipore filter after spraying, the filter cake was washed with ethanol and pressed to dry to obtain a super refined canthaxanthin powder filter cake; such filter cake was mixed with 1 L water solution which contains 0.5 g iso-vitamin C and 76.1 g Arabic gum, stirred and pulped, then put it in a high pressure homogenizer for 4 hours when the emulsion desolventized first in vacuum, and then 100 g canthaxanthin microcapsule containing 23.4 g canthaxanthin was obtained after spray drying.

100 g canthaxanthin microcapsule was mixed with 300 g sunflower seed oil containing 0.4 g BHT and the mixture was grinded in a colloid mill for 3 times in a nitrogen atmosphere at 20° C. to obtain a uniform oil-dispersible canthaxanthin preparation which contains 5.62% canthaxanthin, wherein the average particle size of canthaxanthin was up to 0.83 μm.

Embodiment 4

15 kg lycopene crystal and 120 kg dichloromethane were grinded in a sand mill to obtain a lycopene suspension liquid with a particle size of 3.6 μm; 0.3 kg iso-vitamin C sodium and 85.3 kg octenyl succinic starch ester were dissolved in 200 kg water and kept warm at 40° C. for later use.

The lycopene suspension liquid was fed into the bottom of a 4 L, 4-storeyed stirring vessel with height-diameter ratio of 4 via a pulp pump at a flow rate of 7 kg/h, dichloromethane which is preheated to 37° C. by a coiler preheater was fed into the bottom of the stirring vessel at a flow rate of 180 kg/h as well at the same time, temperature in the vessel was kept at 38° C. and pressure was kept at 0.27 Mpa, stayed for about 12 min and a sample was taken for analysis to know that the dissolution into lycopene solution has been completed; the lycopene solution and isopropanol (at a flow rate of 1000 kg/h) were led into an over-gravity rotary bed crystallization device at the same time and the rotating speed was controlled at 3000 revolution/min to obtain a lycopene dispersion liquid at a flow rate of 1200 kg/h; and then such lycopene dispersion liquid was decompressed in a falling-film evaporator to remove most solvents to obtain a lycopene isopropanol dispersion liquid at a flow rate of 7.5 kg/h.

The above lycopene isopropanol dispersion liquid was led into another over-gravity rotary bed pulping device with pump at a flow rate of 8 kg/h, and the prepared octenyl succinic starch ester solution was fed into such over-gravity rotary bed pulping device at a flow rate of 26 kg/h at the same time to obtain a pulp fluid at a flow rate of around 34 kg/h; spray drying for the pulp fluid was directly conducted to obtain 100 kg lycopene microcapsule which contains 14.4 kg lycopene.

100 kg lycopene microcapsule was mixed with 200 kg peanut oil containing 0.2 kg TBHQ and the mixture was grinded in a colloid mill for 3 times in a nitrogen atmosphere at 20° C. to obtain a uniform oil-dispersible lycopene preparation which contains 4.62% lycopene, wherein the average particle size of lycopene was up to 0.10 μm.

Embodiment 5

40 g lutein coarse crystal was dissolved in 2 L chloroform to make lutein solution; the lutein solution was slowly added into a vessel containing 20 L ethanol in spraying form and the spraying speed was adjusted to make the particle size of precipitated amorphous lutein particles less than 2 μm; a 0.3 μm millipore filter was used after spraying, the filter cake was washed with ethanol and pressed to dry to obtain a super refined lutein powder filter cake; such filter cake was mixed with 1 L water solution which contains 0.3 g iso-vitamin C and 83.3 g Arabic gum, stirred and pulped, then put in a high pressure homogenizer for 4 hours when the emulsion desolventized first in vacuum, and then 100 g lutein microcapsule containing 16.4 g lutein was obtained after spray drying.

100 g lutein microcapsule was mixed with 350 g salad oil containing 0.5 g BHT and the mixture was grinded in a colloid mill for 4 times in a nitrogen atmosphere at 25° C. to obtain a uniform oil-dispersible lutein preparation which contained 3.61% lutein, wherein the average particle size of lutein was up to 0.73 μm.

Embodiment 6

20 g astaxanthin coarse crystal was dissolved in 3 L dichloromethane to make astaxanthin solution; the astaxanthin solution was slowly added into a vessel containing 20 L ethanol in spraying form and the spraying speed was adjusted to make the particle size of precipitated amorphous astaxanthin particles less than 2 μm; filtered with a 0.3 μm millipore filter after spraying, the filter cake was wash with ethanol and pressed to dry to obtain a super refined astaxanthin powder filter cake; such filter cake was mixed with 1 L water solution which contains 0.1 g vitamin C and 89.4 g gelatin, stirred and pulped, then put it in a high pressure homogenizer for 5 hours when the emulsion desolventized first in vacuum, and then 100 g astaxanthin microcapsule containing 10.5 g astaxanthin was obtained after spray drying.

100 g astaxanthin microcapsule with 400 g soybean oil containing 0.1 g tocopherol were mixed and the mixture was grinded in a colloid mill for 1 time in a nitrogen atmosphere at 30° C. to obtain a uniform oil-dispersible astaxanthin preparation which contained 2.1% astaxanthin, wherein the average particle size of astaxanthin was up to 1.00 μm.

The invention claimed is:

1. A method for preparing an oil-dispersible carotenoid preparation, comprising:
    mixing 100 parts by weight of carotenoid microcapsule, 100-400 parts by weight of vegetable oil and 0.1-1 part by weight of antioxidant B, and grinding the mixture in a colloid mill in a nitrogen atmosphere at 10-30° C. to obtain a uniform oil-dispersible carotenoid preparation containing carotenoid particles;
    wherein an average particle size of the carotenoid is 0.1-1 μm;
    wherein the 100 parts by weight of carotenoid microcapsule contains 10.5-35.8 parts by weight carotenoid, 0.1-1 part by weight of antioxidant A and the remaining is a water-soluble colloid;
    the antioxidant A is vitamin C, vitamin C sodium, iso-vitamin C or iso-vitamin C sodium;
    the antioxidant B is tocopherol, ethoxyquin, BHT or TBHQ; and
    wherein a water-soluble colloid protective layer surrounds an outer surface of each of the carotenoid particles.

2. The method for preparing the oil-dispersible carotenoid preparation according to claim 1, wherein the carotenoid is beta-carotene, astaxanthin, lycopene, canthaxanthin or lutein.

3. The method for preparing the oil-dispersible carotenoid preparation according to claim 1, wherein the water-soluble colloid is gelatin, octenyl succinic starch ester or Arabic gum.

4. The method for preparing the oil-dispersible carotenoid preparation according to claim 1, wherein the vegetable oil is soybean oil, corn oil, sunflower seed oil, or peanut oil.

5. An oil-dispersible carotenoid preparation prepared by the method for preparing the oil-dispersible carotenoid preparation according to claim 1.

6. The method of claim 1, wherein the oil-dispersible carotenoid preparation is thermally stable for at least 72 hours at 90° C.

7. The method of claim 1, wherein the average particle size of the carotenoid is 0.1 μm.

8. A method for preparing an oil-dispersible carotenoid preparation, consisting of:
    mixing 100 parts by weight of carotenoid microcapsule, 100-400 parts by weight of vegetable oil and 0.1-1 part of antioxidant B, and grinding the mixture in a colloid mill in a nitrogen atmosphere at 10-30° C. to obtain a uniform oil-dispersible carotenoid preparation containing carotenoid particles wherein an average particle size of the carotenoid is 0.1-1 μm;
    wherein the 100 parts by weight of carotenoid microcapsule contains 10.5-35.8 parts by weight carotenoid, 0.1-1 part by weight of antioxidant A and the remaining is a water-soluble colloid;
    the antioxidant A is vitamin C, vitamin C sodium, iso-vitamin C or iso-vitamin C sodium; the antioxidant B is tocopherol, ethoxyquin, BHT or TBHQ; and
    wherein a water-soluble colloid protective layer surrounds an outer surface of each of the carotenoid particles.

* * * * *